US010456366B2

(12) United States Patent
Chiou

(10) Patent No.: US 10,456,366 B2
(45) Date of Patent: Oct. 29, 2019

(54) COMPOSITION AND METHODS FOR TISSUE REGENERATION

(71) Applicant: Win L. Chiou, Burr Ridge, IL (US)

(72) Inventor: Win L. Chiou, Burr Ridge, IL (US)

(73) Assignee: Chiou Consulting, Inc., Burr Ridge, IL (US)

( * ) Notice: Subject to any disclaimer, the term of this patent is extended or adjusted under 35 U.S.C. 154(b) by 0 days.

(21) Appl. No.: 15/826,266

(22) Filed: Nov. 29, 2017

(65) Prior Publication Data

US 2019/0160022 A1   May 30, 2019

(51) Int. Cl.
| | |
|---|---|
| A61K 31/047 | (2006.01) |
| A61K 9/00 | (2006.01) |
| A61K 9/08 | (2006.01) |
| A61K 8/34 | (2006.01) |
| A61Q 11/00 | (2006.01) |
| A61K 33/14 | (2006.01) |
| A61K 33/06 | (2006.01) |
| A61K 31/198 | (2006.01) |
| A61K 36/886 | (2006.01) |
| A61K 31/4188 | (2006.01) |
| A61Q 3/00 | (2006.01) |
| A61K 8/368 | (2006.01) |
| A61K 8/20 | (2006.01) |
| A61K 8/23 | (2006.01) |
| A61K 8/44 | (2006.01) |
| A61K 8/67 | (2006.01) |
| A61K 8/73 | (2006.01) |
| A61K 8/04 | (2006.01) |
| A61Q 7/00 | (2006.01) |
| A61K 8/9794 | (2017.01) |
| A61Q 5/02 | (2006.01) |
| A61K 31/60 | (2006.01) |

(52) U.S. Cl.
CPC ............ *A61K 31/047* (2013.01); *A61K 8/042* (2013.01); *A61K 8/20* (2013.01); *A61K 8/23* (2013.01); *A61K 8/345* (2013.01); *A61K 8/368* (2013.01); *A61K 8/44* (2013.01); *A61K 8/673* (2013.01); *A61K 8/73* (2013.01); *A61K 8/9794* (2017.08); *A61K 9/0014* (2013.01); *A61K 9/08* (2013.01); *A61K 31/198* (2013.01); *A61K 31/4188* (2013.01); *A61K 31/60* (2013.01); *A61K 33/06* (2013.01); *A61K 33/14* (2013.01); *A61K 36/886* (2013.01); *A61Q 3/00* (2013.01); *A61Q 5/02* (2013.01); *A61Q 7/00* (2013.01); *A61Q 11/00* (2013.01)

(58) Field of Classification Search
None
See application file for complete search history.

(56) References Cited

U.S. PATENT DOCUMENTS

| | | | | |
|---|---|---|---|---|
| 3,574,824 A | * | 4/1971 | Echeandia et al. | ...... A61K 8/24 424/50 |
| 4,139,619 A | * | 2/1979 | Chidsey, III | ............. A61Q 7/00 424/45 |
| 5,004,599 A | * | 4/1991 | Scher | ..................... A61K 8/671 424/61 |
| 5,166,168 A | * | 11/1992 | Stiefel | ................. A61K 31/415 514/387 |
| 5,578,294 A | * | 11/1996 | Lukacovic | ............. A61K 8/365 424/49 |
| 5,631,000 A | * | 5/1997 | Pellico | .................... A61K 8/042 424/53 |
| 5,723,106 A | * | 3/1998 | Buch | ........................ A61K 8/34 424/49 |
| 7,258,875 B2 | | 8/2007 | Chiou | |
| 2003/0028169 A1 | * | 2/2003 | Fossel | .................. A61K 8/0208 604/500 |
| 2004/0101497 A1 | * | 5/2004 | Montgomery | ........... A61K 8/22 424/53 |
| 2010/0087403 A1 | * | 4/2010 | Chiou | .................. A61K 9/0014 514/164 |
| 2011/0183011 A1 | * | 7/2011 | Chiou | .................. A61K 9/0014 424/682 |
| 2013/0045457 A1 | * | 2/2013 | Chetiar | ................ A61N 5/0601 433/29 |

FOREIGN PATENT DOCUMENTS

| | | | |
|---|---|---|---|
| CN | 1857268 A | * 11/2006 | |
| WO | WO-8401693 A1 | * 5/1984 | ............... A23G 4/06 |

OTHER PUBLICATIONS

English Translation of CN 1857268 A. Obtained from https://patents.google.com/patent/CN1857268A/en?oq=minoxidil+propylene+glycol on Dec. 3, 2018. Originally published in Chinese on Nov. 8, 2006. 5 printed pages. (Year: 2006).*

B. Galliot et al., Trends in tissue repair and regeneration, Development (2017) 144: 357-364.

W. L. Chiou, Aging Kinetics of Human Hearts and Skin: New Aging Theories and Implications in the Use of Sunscreens, Scientific Pages Dermatol. (2017) 1(1): 1-5.

* cited by examiner

*Primary Examiner* — Isaac Shomer
(74) *Attorney, Agent, or Firm* — Merchant & Gould P.C.

(57) ABSTRACT

Described herein are topical compositions containing an effective amount of propylene glycol, as a sole active ingredient or a principal active ingredient, and a pharmaceutically acceptable medium. Also described herein are methods of promoting the growth of or the regeneration of a tissue such as nail, hair, gum and skin in humans by topically administering the topical compositions to a human in need thereof.

4 Claims, No Drawings

COMPOSITION AND METHODS FOR TISSUE REGENERATION

FIELD OF THE INVENTION

Described herein are topical compositions containing an effective amount of propylene glycol, as a sole active ingredient or a principal active ingredient, and a pharmaceutically acceptable medium. Also described herein are methods of promoting the growth of or the regeneration of a tissue such as nail, hair, gum and skin in humans by topically administering the topical compositions to a human in need thereof.

BACKGROUND OF THE INVENTION

Although extremely extensive research on tissue regeneration has been carried out worldwide in the last many decades, it appears that to date there are no commercial topical products available to regenerate tissues such as nails and gums. This invention discloses a totally surprising and extremely unexpected discovery that preparations containing an effective amount of a sole active or a principal active ingredient, propylene glycol (PG), a small water-mixable molecule and a known natural metabolite in humans, can be topically applied to promote the growth of or to regenerate vastly different tissues such as nails, gums, hairs and skin.

The use to regenerate gum tissue may be particularly significant. This is because the gum recession, generally being considered as an irreversible aging process, is a common and serious problem especially in elderly adults. It may result in loosening and loss of teeth and negatively affect the quality of life. Treatments with dental implant or use of artificial teeth are expensive. Although some herbal products purportedly claimed to be useful for helping grow gums are available, there is an urgent need to find a simple, safe, effective method to regenerate gum tissue or to slow down gum recession.

The exact reason for these astonishing findings is unknown and their potential mechanisms are, undoubtedly extremely complicated especially at molecular levels (B. Galliot et al., Development, 144:357-364, 2017 and references therein). However, this may be simply speculated to be directly or indirectly attributed to rejuvenation of their tissue stem/progenitor cells. See W. L. Chiou, Scient Pages Dermatol. 1: 1-5, 2017 and references therein.

PG is often used as a solvent in cosmetics and drugs. PG could treat acne in humans (W. L. Chiou, U.S. Pat. No. 8,846,646, 2014), and could even serve as a universal microbicide to treat a wide variety of other topical infections (W. L. Chiou, U.S. Pat. No. 8,513,225, 2013).

To date, PG is still commonly and mistakenly regarded as a highly undesirable ingredient in skincare products (W. L. Chiou, U.S. Pat. No. 8,513,225, 2013). It is, in fact, a very safe compound when used properly. For example, rats fed with water containing 10% of PG and dogs fed with food containing 8% of PG for two years have been shown to cause no adverse effects. It is generally regarded as safe (GRAS).

SUMMARY OF THE INVENTION

A very surprising, totally unexpected, and highly useful compositions and methods to reduce or prevent aging of a tissue, enhance the growth of a tissue, to repair a damaged tissue and/or to regenerate a new tissue in mammals are disclosed herein. The method comprises (consists essentially of or consists of) topical delivery of an effective amount of PG as a sole or major active ingredient to the tissue to be treated as a uniformly applied layer from a pharmaceutically acceptable medium/preparation at an appropriate time interval. PG concentrations may range from about 1% to about 99% by weight (w/w). It may also range from about 3% to about 99% or from about 5% or 10% to about 95% or from about 20% to about 95%, or about 30% to about 95%, or from about 40% to about 95% or about 50% or about 60% to about 95% (w/w).

Commonly known cell-growth-promoting agents such as glycerin, aloe vera, aloe vera gel, biotin, dimethyl sulfoxide, arginine or its salt, zinc chloride, sodium chloride and magnesium chloride or sulfate, N-acetylcysteine, and glutathione may also be added to the PG-containing composition at concentrations ranging from about 0.001% to about 30% (w/w) so as to enhance efficacy of the PG-containing composition. Potential absorption enhancers such as aloe vera, aloe vera gel, dimethyl sulfoxide, salicylic acid, sodium salicylate, citric acid, lactic acid and glycolic acid may also be added to the PG-containing composition at concentrations ranging from about 0.001% to about 30% (w/w).

Salicylic acid or its salts such as sodium salicylate as well as dimethyl sulfoxide are also known to have anti-inflammatory and analgesic effects. They are also known to improve skin thickness, collagen production and wound healing. Therefore, it is contemplated to use salicylic acid or its salts or dimethyl sulfoxide as an optional ingredient in the PG-containing compositions disclosed herein.

Addition of glycerin to high concentrations of PG could reduce or eliminate its possible irritating effect on skin (W. L. Chiou, U.S. Pat. No. 8,846,646, 2014). Also, glycerin has a sweet taste and is therefore useful to gum composition. The concentration of glycerin used in the present invention can be up to about 80% (w/w). Obviously, water or other inert solvents such as polyethylene glycol 400 can also be added. Without the presence of an absorption enhancer, glycerin, an extremely polar compound, is known to be very slowly absorbed into skin, and probably also scalp, nail and gum.

Buffering agents, electrolytes, surfactants, gelling or viscosity-enhancing agents (thickeners), and flavoring and coloring agents, as well as preservatives and aerosol propellants may also be used. Other water-soluble vitamins such as vitamin C and riboflavin may also be added to the PG-containing compositions described herein. The dosage forms may include, but are not limited to, liquid solutions, liquid mixture, emulsions, suspensions, gels, hydrogels, creams, pastes, lotions, aerosols, sprays, and dressings. The preparation can be applied once a day or multiple times a day or at an appropriate time interval.

The tissue to be treated can be any tissue in the body such as scalp, nails, gums, skin, burned skin, burned tissue, wounded tissue, eyebrow, eyelash and mucous membrane. Potential applications of the PG-containing compositions described herein for rejuvenations of whole organs, stem cells, progenitor cells or somatic cells in vivo or in vitro remain to be explored; for somatic cells rejuvenation (reprogramming) may result or help result in their conversion into induced pluripotent cells. The PG-compositions described herein may also be used as a carrier or vehicle for stem cells or progenitor cells in clinical therapy.

After injury, damaged nails often stop growing for months or years. It appears that to date no drug products are available to regenerate new nails.

Example 1 describes the surprising results of regeneration of new healthy toenails observed in humans after daily application of a PG-containing composition. Example 2 describes that a PG-containing composition resulted in marked acceleration of nail growth. Further, Example 3 describes an alternative PG-containing composition for toe nails and finger nails.

The PG-containing compositions described herein can also grow new hair in persons with minor problems of hair thinning and loss (Example 4) or with severe hair loss (Example 5). Hair graying may also be corrected. It can also be used as a hair wash gel (Example 6).

The PG-containing compositions described herein may also be particularly valuable to treat burned skin or tissue to promote re-growth of new skin or new tissue (Example 7). Since aging is known to result in thinning of skin, thus PG-containing compositions may also be useful to combat skin aging by increasing growth of new skin. It should be highly useful to treat wounded skin or tissue without the need of using conventional antibiotics (Example 8). The PG-containing compositions are particularly useful to treat or prevent gum recession (Examples 8 to 12).

DETAILED DESCRIPTION OF THE INVENTION

A first embodiment is directed to a topical composition for reducing or preventing the gum recession or promoting the gum growth or regenerating new gum in a human comprising: a gum-growth-promoting agent consisting of from about 1% to about 99% by weight of propylene glycol and a pharmaceutically acceptable medium; wherein the topical composition is to be applied to the gum area as a uniform layer, preferably at least once a day before bedtime, or to be injected topically into various gum areas at an appropriate time interval, wherein the composition is selected from the group consisting of a liquid solution, liquid mixture, suspension, lotion, paste, gel, cream, foam, spray, dressing and an emulsion.

In a first aspect of the first embodiment, the concentration of propylene glycol in the composition ranges from about 3% to about 95% by weight or about 10% to about 95% by weight.

In a second aspect of the first embodiment, the concentration of propylene glycol in the composition ranges from about 20% to about 95% by weight or about 30% to about 95% by weight.

In a third aspect of the first embodiment, the concentration of propylene glycol in the composition ranges from about 40% to about 95% by weight.

In a fourth aspect of the first embodiment, the pharmaceutically acceptable medium contains an ingredient selected from the group consisting of water, glycerin, dimethyl sulfoxide, other solvent, an electrolyte, a pH modifier, a surfactant, an absorption enhancer, an emulsifier, a thickener, a fragrance, a color, a preservative, and combinations thereof.

A fifth aspect of the first embodiment is directed to a method for reducing or preventing the gum recession or promoting the gum growth or regenerating new gum in a human comprising: administering to the gum of the human in need thereof an effective amount of the composition of the first embodiment.

As related to the fifth aspect of the first embodiment, the administering may occur on an as needed basis. Alternatively, the administering may occur once per day or at least once per day. When administered on a daily basis, the administering may occur once per day, twice per day, three times per day, four times a day, or combinations thereof over an extended period of time so as to achieve the desired result of either reducing or preventing the gum recession or promoting the gum growth or new gum regeneration.

A second embodiment is directed to a method for enhancing the growth of and/or for regenerating of a topical tissue in a human, said method comprised of applying to the human in need thereof a composition comprising: an effective concentration of propylene glycol and a pharmaceutically acceptable medium containing an ingredient selected from the group consisting of water, glycerin, dimethyl sulfoxide a solvent, electrolyte, pH modifier, surfactant, absorption enhancer, emulsifier, thickener, fragrance, preservative, salicylic acid, sodium salicylate, an emulsifier and combination thereof, and, optionally, a cell-growth promoter; wherein the composition is selected from the group consisting of a liquid solution, liquid mixture, suspension, lotion, paste, gel, cream, foam, spray, dressing and an emulsion; and wherein the dosage form is applied topically to the tissue of the human to be treated.

As related to the second embodiment, the applying may occur on an as needed basis. Alternatively, the applying may occur once per day or at least once per day. When applied topically on a daily basis, the applying may occur once per day, twice per day, three times per day, four times a day, or combinations thereof over an extended period of time so as to achieve the desired result of either enhancing the growth of and/or for regenerating of a topical tissue in a human.

In a first aspect of the second embodiment, wherein the topical tissue is a scalp.

In a second aspect of the second embodiment, the topical tissue is an eyebrow, an eyelash, or a skin or a wounded skin.

In a third aspect of the second embodiment, the topical tissue is a burned skin.

In a fourth aspect of the second embodiment, the topical tissue is a nail.

In a fifth aspect of the second embodiment, the composition contains the cell-growth promoter in an amount that ranges from about 0.001% to about 30% by weight, wherein the cell-growth promoter is selected from the group consisting of biotin, one or more other water-soluble vitamins, aloe vera powder, aloe vera gel, arginine, arginine hydrochloride, dimethyl sulfoxide, sodium chloride, zinc chloride, magnesium chloride, magnesium sulfate, salicylic acid, sodium salicylate, and combinations thereof.

One of ordinary skill will appreciate that water-soluble vitamins, include, for example, Riboflavin, Pyridoxin, Biotin, Sodium Ascorbate and Thiamine.

The expression "by weight" or ("w/w") is based on the total weight of the composition.

The compositions and methods described herein are illustrated by the following examples. The examples should not be used to limit the scope of the claims presented herein.

EXAMPLE 1

Dramatic Regeneration of New Healthy Toenails after Nail Injuries by a composition containing 80% of PG, 10% of Glycerin, 0.5% of Sodium Salicylate, 0.1% of Sodium Chloride, 0.05% of Magnesium Sulfate, 0.01% of Arginine, 0.01% of Aloe Vera Powder, 0.0001% of Biotin (w/w), and Water (q.s.) in Humans.

The above solution was applied as a uniform layer to darkened, non-growing injured toenails twice a day in one adult (one big toenail affected) and about 4 times a day in the other adult (one big toenail and two other small toenails affected). Healthy new nails were grown out in about 4 months. Two new healthy toenails were also quickly regenerated in one adult after about 5 months of daily applications of the solution. The above results are believed to be the first of its kind ever reported. All concentrations used in this application are based on weight.

EXAMPLE 2

Acceleration of Nail Growth by a Solution Described in Example 1 or by a Gel Prepared with an Addition of 1% of Xanthan Gum, a gelling agent.

To serve as a base line a commercial red nail polish was applied as a thin layer to the cuticle area of the two big toenails of an adult. The above gel was then applied to the left big toenail 2 to 4 times a day. After about 2 months the nail was found to grow about 50% faster from the treated nail compared with the untreated nail. This was repeated about 8 months later with the left toenail serving a control. The right toenail was found to grow about 41% faster compared with the control nail. This kind of enhanced growth of toenail was also found in several other adults using the solution preparation.

Much lower concentrations of PG such as 10% or 20% or 30% may also be used. On the other hand, a preparation containing 95% of PG and 5% of glycerin may also be employed to safely and effectively regenerate new nails.

EXAMPLE 3

A Gel Containing 20% of PG, 5% of Arginine, 0.001% of Biotin, 1% of Xanthan Gum and Water (q.s.) for Nail Regeneration or Acceleration of Nail Growth in Humans.

EXAMPLE 4

Promotion of Hair Growth in Men by an Aqueous Solution Containing 70% of PG, 10% of Glycerin, 3% of Sodium Salicylate, 0.01% of Magnesium Sulfate, 3% of Sodium Chloride and Water (q.s.)

The above solution was applied twice daily from a spray bottle to the scalp of two adults who were losing their hair. New healthy, thicker, dark hair was found to start to grow in about one week. The length of new hair was about two centimeters in about one month. The rapidity of hair growth in this preliminary study seemed quite encouraging compared with much slower (probably 6 to 12 months) growth rate of some commercial FDA-approved products.

EXAMPLE 5

Hair Regeneration in a Man with Male Baldness Pattern Following Daily Topical Applications of an Aqueous Solution Containing 60% of PG, 10% of Glycerin, 10% of dimethyl Sulfoxide, 2% of Sodium Salicylate, 4% of Sodium Chloride, 0.7% of N-acetylcysteine, 0.3% of Sodium Phosphate Monobasic, 0.05% of Magnesium Sulfate, 1.5% of Arginine HCl, 1% of Arginine, 0.2% of Glutathion, 0.001% of Biotin and Water (q.s.)

A male at age 79 (Applicant) applied the above solution twice daily to the right side of his scalp. In about one month new black hair was found to start growing in the applied right side while the controlled left side did not show visible growth of new hair. The above study is still on-going at the time of preparation of this patent application. It is noted that old hair was largely gray and most new hair is dark.

EXAMPLE 6

Hair Wash Gel Containing 10% of PG, 10% of Glycerin, 1% of Xanthan Gum, 0.9% of Sodium Chloride, Traces of Water-Soluble Vitamins (such as Riboflavin, Pyridoxin, Biotin, Sodium Ascorbate and Thiamine) and Water (q.s.).

EXAMPLE 7

Compositions and Method for Treating Burned or Wounded Skin

An aqueous solution containing 45% of PG, 35% of glycerin, 1% of sodium salicylate, 0.9% of sodium chloride, 0.5% of Arginine, 0.1% of magnesium sulfate, 0.1% of ascorbic acid and 17.4% of water is prepared. This solution can be applied as a thin layer from a soft brush or spray bottle to the burned or wounded skin surface followed by coverage of a proper dressing. This may be repeated twice a day for several days. Healing or re-growth of skin is then expected probably without scarring. An alternative formula will contain only 25% of PG.

A gel containing 80% of PG, 10% of glycerin, 2% of sodium salicylate, 1% of Xanthan Gum and Water (q.s.). was applied to a superficial wounded skin, about 0.2×5 cm in size, on the forearm of an adult once a day for three days. The wound was healed later without infection.

EXAMPLE 8

Dramatic Gum Regeneration and Stabilization of a Loose Tooth by a Gel Containing 70% of PG, 10% of Glycerin, 0.5% of Aloe Vera Powder, 1% of Xanthan Gum and Water (q.s.) in an Adult.

About a teaspoon of the above gel was applied into the mouth of a male senior with a severe gum loss and with one loose tooth each night after teeth cleaning before bed-time. This was followed by a swirling motion for about one minute in order to mix the gel with the saliva and to have the mixture reach various gum areas. The study lasted about two months. Gum pictures taken before and after treatment in a local dental office revealed surprising healthy growth of new gum. Most importantly, the test subject felt that the earlier loose tooth became much steadier and stronger. No irritation or discomfort was reported. The dentist was so impressed with the gum regeneration and offered to become a volunteer to test the gel because of her receding gum problem.

EXAMPLE 9

A Gel Containing 50% of PG, 10% of Glycerin, 10% of Dimethyl Sulfoxide, 0.5% of Sodium Chloride, 0.5% of Aloe Vera Gel, 0.5% of Sodium Ascorbate, 0.001% of Biotin and Water (q.s.) for Regeneration of Gum in Humans

EXAMPLE 10

A Toothpaste Formula for Promoting Gum Growth: 15% of PG, '10% of Glycerin, 3% of Titanium Dioxide, 0.9% of Sodium Chloride, 0.00001% of Riboflavin, 0.1% of Arginine, 0.3% of Sodium Stearate, 0.05% of Magnesium Sulfate, 0.001% of Peppermint, 2% of Xanthan Gum and Water (q.s.)

It is to be noted that 3, 5, 10, or 25% of PG can also be used in the above formula.

EXAMPLE 11

A Mouth Wash Solution Containing 20% of PG, 10% of Glycerin, 0.3% of Sodium Chloride, 0.1% of Magnesium Chloride, Trace of Fragrance (Such as Peppermint) and Water (q.s.) for Promotion of Gum Growth in the mouth.

EXAMPLE 12

A Solution Containing 60% of PG, 10% of Glycerin, 0.9% Sodium Chloride and Water (q.s.) for Microinjection into Various Parts of Anesthetized Gum by a Dentist at an Appropriate Interval.

It is possible that high concentrations of glycerin such as 80% with 10% of PG and 10% of normal saline may also be injected directly to gums for promoting gum regeneration.

The above examples are intended to be illustrative, and not restrictive. One skilled in the art will be able to ascertain, without any more routine experimentation, many references to specific embodiments described herein. These equivalents are intended to be encompassed by the following claims.

What is claimed is:

1. A method for reducing gum recession or promoting gum growth in a human in need thereof comprising:
    administering to the gum of the human in need thereof an effective amount of a topical composition comprising:
    a) a gum-growth-promoting agent consisting of from about 10% to about 95% by weight of propylene glycol;
    b) a pharmaceutically acceptable medium; and
    c) optionally, a cell-growth promoter;
    wherein said administering comprises applying the topical composition to the gum area as a uniform layer or injecting topically into various gum areas providing for absorption of a gum receding or gum growth promoting amount of propylene glycol by the gum.

2. The method of claim 1, wherein the concentration of propylene glycol ranges from about 30% to about 95% by weight.

3. The method of claim 1, wherein the pharmaceutically acceptable medium contains one or more of the following ingredients: water, glycerin, dimethyl sulfoxide, other solvent, an electrolyte, a pH modifier, a surfactant, an absorption enhancer, an emulsifier, a thickener, a fragrance, a color, and a preservative.

4. The method of claim 1, wherein the topic composition is a liquid solution, a liquid mixture, a suspension, a lotion, a paste, a gel, a cream, a foam, a spray, a dressing, or an emulsion.

* * * * *